(12) United States Patent
Elliott et al.

(10) Patent No.: US 6,859,353 B2
(45) Date of Patent: Feb. 22, 2005

(54) CAPACITOR INTERCONNECT DESIGN

(75) Inventors: William B. Elliott, Alden, NY (US); Eric Stemen, Lancaster, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 0 days.

(21) Appl. No.: 10/734,051

(22) Filed: Dec. 11, 2003

(65) Prior Publication Data

US 2004/0120099 A1 Jun. 24, 2004

Related U.S. Application Data

(60) Provisional application No. 60/434,797, filed on Dec. 18, 2002, and provisional application No. 60/433,684, filed on Dec. 16, 2002.

(51) Int. Cl.[7] ................................. H01G 2/10

(52) U.S. Cl. ..................... 361/517; 361/520; 29/25.41; 607/5

(58) Field of Search ........................... 361/301.3, 301.4, 361/306.1, 327, 517, 520, 522, 531, 535–537, 541; 29/25.41, 25.42; 607/5

(56) References Cited

U.S. PATENT DOCUMENTS

| | | |
|---|---|---|
| 5,825,639 A | 10/1998 | Wagoner |
| 2002/0180268 A1 | 12/2002 | Mattes |

*Primary Examiner*—Anthony Dinkins
(74) *Attorney, Agent, or Firm*—Michael F. Scalise

(57) ABSTRACT

Structures for serially connecting at least two capacitors together are described. Serially connecting capacitors together provides device manufactures, such as those selling implantable medical devices, with broad flexibility in terms of both how many capacitors are incorporated in the device and what configuration the capacitor assembly will assume.

20 Claims, 9 Drawing Sheets

US 6,859,353 B2

CAPACITOR INTERCONNECT DESIGN

CROSS-REFERENCE TO RELATED APPLICATIONS

The present application claims priority based upon provisional application Ser. Nos. 60/433,684 filed Dec. 16, 2002, and 60/434,797 filed Dec. 18, 2002.

BACKGROUND OF THE INVENTION

The present invention generally relates to a capacitor and, more particularly, to at least two side-by-side capacitors connected in series.

SUMMARY OF THE INVENTION

As more and more medical applications are investigated and implemented to aid and assist the human body, devices needed to deliver the desired therapy are becoming increasingly more sophisticated, both functionally and in terms of their structural makeup. Modern implantable devices require power sources that are smaller in size, but powerful enough to meet the therapy requirements. For example, a cardiac defibrillator has a battery powering circuits performing such functions as, for example, the heart sensing and pacing functions. This requires electrical current of about 1 microampere to about 100 milliamperes. From time-to-time, the cardiac defibrillator may require a generally high rate, pulse discharge load component that occurs, for example, during charging of a capacitor assembly in the defibrillator for the purpose of delivering an electrical shock to the heart to treat tachyarrhythmias, the irregular, rapid heartbeats that can be fatal if left uncorrected. This requires electrical current of about 1 ampere to about 4 amperes.

The current trend in medicine is to make cardiac defibrillators, and like implantable devices, as small and lightweight as possible without compromising power. This, in turn, means that capacitors contained in these devices must be readily adaptable in how they are connected to each other as well as to the battery and the device circuitry. In that light, the present invention relates to structures for serially connecting at least two capacitors together to provide the device manufacture with broad flexibility in terms of both how many capacitors are incorporated in the device and what configuration the capacitor assembly will assume.

These and other aspects of the present invention will become more apparent to those skilled in the art by reference to the following description and to the appended drawings.

DETAILED DESCRIPTION OF THE PREFERRED EMBODIMENTS

Figure 1:
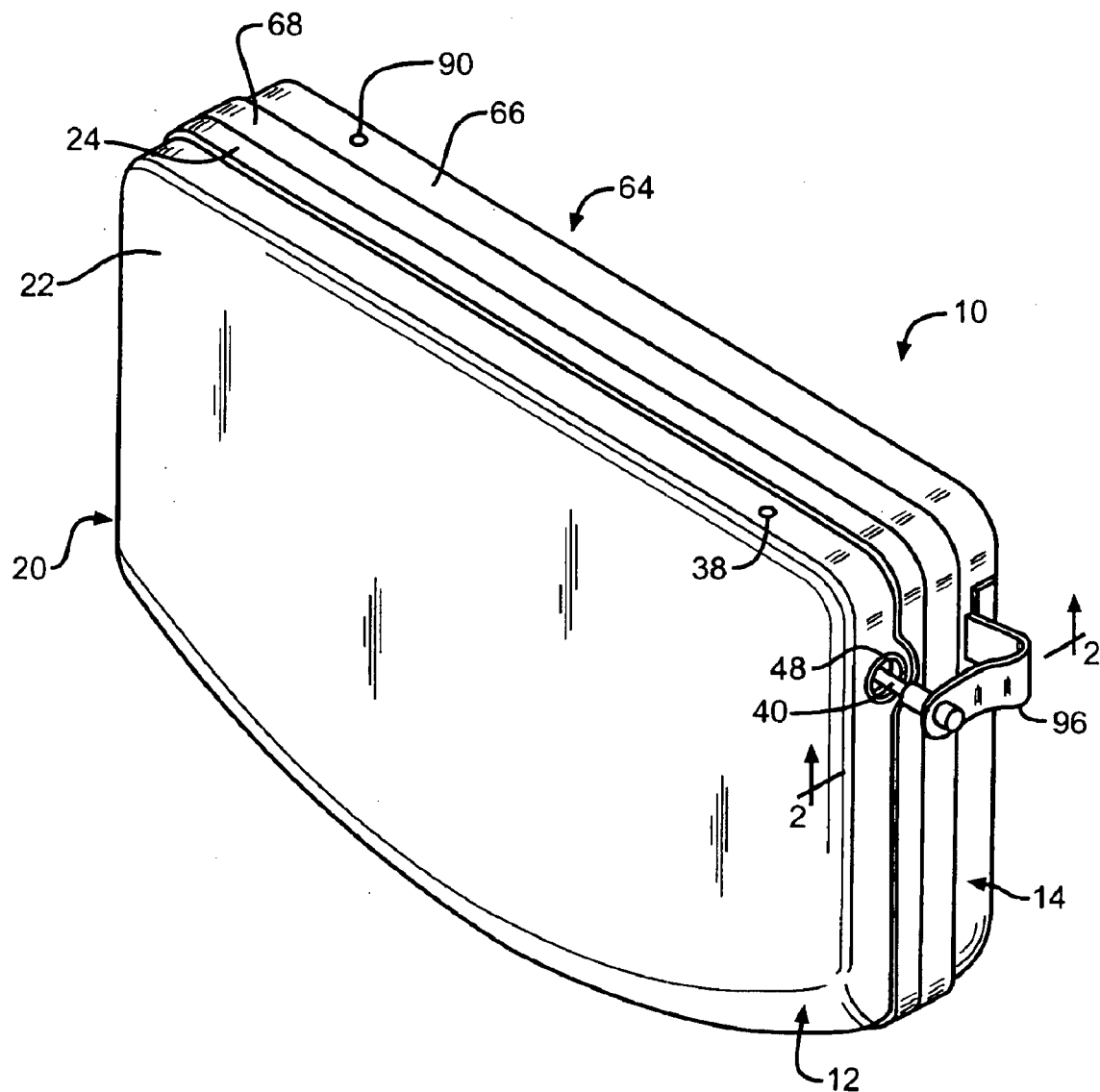
FIG. 1 is a perspective view looking at the right edges of two side-by-side capacitors connected in series according to the present invention.

Referring now to the drawings, FIGS. 1, 5, 8 and 9 are perspective views showing various embodiments of side-by-side capacitors connected in series according to the present invention. As shown in FIGS. 1 to 4, 8 and 9, a first embodiment of the series connected capacitor assembly 10 comprises a first capacitor 12 and a side-by-side second capacitor 14. The first capacitor 12 comprises an anode of an anode active material 16 and a cathode of a cathode active material 18 (FIG. 4) housed inside a hermetically sealed casing 20. The capacitor electrodes are operatively associated with each other by an electrolyte (not shown) contained inside the casing, as will be described in detail hereinafter. It should be pointed out that the capacitors 12, 14 can be of either an electrochemical type wherein both the anode and the cathode electrodes are provided by conductive substrates having a capacitive material contacted thereto or, an electrolyte type wherein the cathode electrode is provided by a conductive substrate having capacitive properties. The illustrated capacitors are preferably of the latter type, however, that should not be construed as limiting.

As particularly shown in FIGS. 2, 3, 8 and 9, casing 20 is of a metal material comprising mating first and second clamshells or mating casing portions 22 and 24. Casing portion 22 comprises a surrounding sidewall 26 extending to a face wall 28. Similarly, casing portion 24 comprises a surrounding sidewall 30 extending to a face wall 32. The sidewall 26 of the first casing portion 22 is sized to fit inside the periphery of the second sidewall 30 in a closely spaced relationship. This means that the first face wall 28 is somewhat smaller in planar area than the second face wall 32 of casing portion 24. Also, the height of the second surrounding sidewall 30 of casing portion 24 is less than the height of the first surrounding sidewall 26. The surrounding sidewall 26 has an inwardly angled lead-in portion 34 that facilitates mating the casing portions 22, 24 to each other.

With the first and second casing portions 22, 24 mated to each other, the distal end of the second surrounding sidewall 30 contacts the first surrounding sidewall 26 a short distance toward the face 28 from the bend forming the lead-in portion 34. The casing portions 22, 24 are hermetically sealed to each other by welding the sidewalls 26, 30 together at this contact location. The weld is provided by any conventional means; however, a preferred method is by laser welding.

The anode active material 16 is typically of a metal selected from the group consisting of tantalum, aluminum, titanium, niobium, zirconium, hafnium, tungsten, molybdenum, vanadium, silicon, germanium, and mixtures thereof in the form of a pellet. As is well known by those skilled in the art, the anode metal in powdered form, for example tantalum powder, is compressed into a pellet having an anode wire 36 embedded therein and extending there from, and sintered under a vacuum at high temperatures. The porous body is then anodized in a suitable electrolyte to fill its pores with the electrolyte and to form a continuous dielectric oxide film on the sintered body. The assembly is then reformed to a desired voltage to produce an oxide layer over the sintered body and anode wire. The anode can also be of an etched aluminum or titanium foil.

The cathode electrode is spaced from the anode electrode housed inside the casing and comprises the cathode active material 18. The cathode active material has a thickness of about a few hundred Angstroms to about 0.1 millimeters directly coated on the inner surface of the face walls 28, 32 (FIGS. 2 to 4) or, it is coated on a conductive substrate (not shown) in electrical contact with the inner surface of the face walls. In that respect, the face walls 28, 32 may be of an anodized-etched conductive material, have a sintered active material with or without oxide contacted thereto, be contacted with a double layer capacitive material, for example a finely divided carbonaceous material such as graphite or carbon or platinum black, a redox, pseudocapacitive or an under potential material, or be an electroactive conducting polymer such as polyaniline, polypyrol, polythiophene, and polyacetylene, and mixtures thereof.

According to one preferred aspect of the present invention, the redox or cathode active material 18 includes an oxide of a first metal, a nitride of a first metal, a carbonitride of a first metal, and/or a carbide of a first metal, the oxide, nitride, carbonitride and carbide of the first metal having pseudocapacitive properties. The first metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead.

The cathode active material 18 may also include a second or more metals. The second metal is in the form of an oxide, a nitride, a carbonitride or carbide, and is not essential to the intended use of the conductive face walls 28, 32 as a capacitor electrode, and the like. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the invention, the cathode active material 18 includes an oxide of ruthenium or oxides of ruthenium and tantalum.

The mating casing portions 22, 24, and the electrically connected conductive substrate if it is provided, are preferably selected from the group consisting of tantalum, titanium, nickel, molybdenum, niobium, cobalt, stainless steel, tungsten, platinum, palladium, gold, silver, copper, chromium, vanadium, aluminum, zirconium, hafnium, zinc, iron, and mixtures and alloys thereof. Preferably, the face and sidewalls of the casing portions have a thickness of about 0.001 to about 2 millimeters.

The exemplary electrolytic type capacitor shown in FIGS. 1 to 4, 8 and 9 has the cathode active material 18 preferably coating the face walls 28, 32 spaced from the respective sidewalls 26, 30. Such a coating is accomplished by providing the conductive face walls 28, 32 with a masking material in a known manner so that only an intended area of the face walls is contacted with active material. The masking material is removed from the face walls prior to capacitor fabrication. Preferably, the cathode active material 18 is substantially aligned in a face-to-face relationship with the major faces of the anode active material 16.

A preferred coating process is in the form of an ultrasonically generated aerosol as described in U.S. Pat. Nos. 5,894,403; 5,920,455; 6,224,985; and 6,468,605, all to Shah et al. These patents are assigned to the assignee of the present invention and incorporated herein by reference. In that manner, the ultrasonically generated active material contacted to the conductive surfaces has a majority of its particles with diameters of less than about 10 microns. This provides an internal surface area for the active material of about 10 m$^2$/gram to about 1,500 m$^2$/gram.

A separator (not shown) of electrically insulative material is provided between the anode active material 16 and the cathode active material 18 to prevent an internal electrical short circuit between them. The separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the capacitor 12. Illustrative separator materials include woven and non-woven fabrics of polyolefinic fibers including polypropylene and polyethylene or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR® (DMS Solutech), a polytetrafluoroethylene membrane commercially available under the designation ZITEX® (Chemplast Inc.), a polypropylene membrane commercially available under the designation CELGARD® (Celanese Plastic Company, Inc.), and a membrane commercially available under the designation DEXIGLAS® (C. H. Dexter, Div., Dexter Corp.). Cellulose based separators also typically used in capacitors are contemplated by the scope of the present invention. Depending on the electrolyte used, the separator can be treated to improve its wettability, as is well known by those skilled in the art.

A suitable electrolyte for the capacitors 12, 14 is described in U.S. Pat. No. 6,219,222 to Shah et al., which includes a mixed solvent of water and ethylene glycol having an ammonium salt dissolved therein. U.S. Pub. Nos. 20030090857 and 20030142464 describe other electrolytes for the present capacitors. The electrolyte of the former publication comprises water, a water-soluble inorganic and/or organic acid and/or salt, and a water-soluble nitro-aromatic compound while the latter relates to an electrolyte having de-ionized water, an organic solvent, isobutyric acid and a concentrated ammonium salt. These publications and patent are assigned to the assignee of the present invention and incorporated herein by reference. The electrolyte is provided inside the hermetically sealed casing through a fill opening closed by a hermetic closure 38 (FIG. 1), as is well known by those skilled in the art.

The casing 20, including the portions 22, 24, being of a conductive metal serves as one terminal for making electrical connection between the capacitor and its load. A pin 40 (FIGS. 2, 8 and 9) is welded to the sidewall 26 to provide the negative terminal for the first capacitor 12. Pin 40 also provides the negative terminal for the side-by-side capacitor assembly 10, as will be described in detail hereinafter.

The other electrical terminal or contact for the first capacitor 12 comprises the anode wire 36 extending from the anode active material 16 and connected to the anode lead 42 extending through the first surrounding sidewall 26. A sleeve 44 is mounted on the distal end of the anode lead 42. The sleeve 44 provides for serially connecting the first capacitor 12 to the second capacitor 14, as will be described in detail hereinafter.

Figure 2:
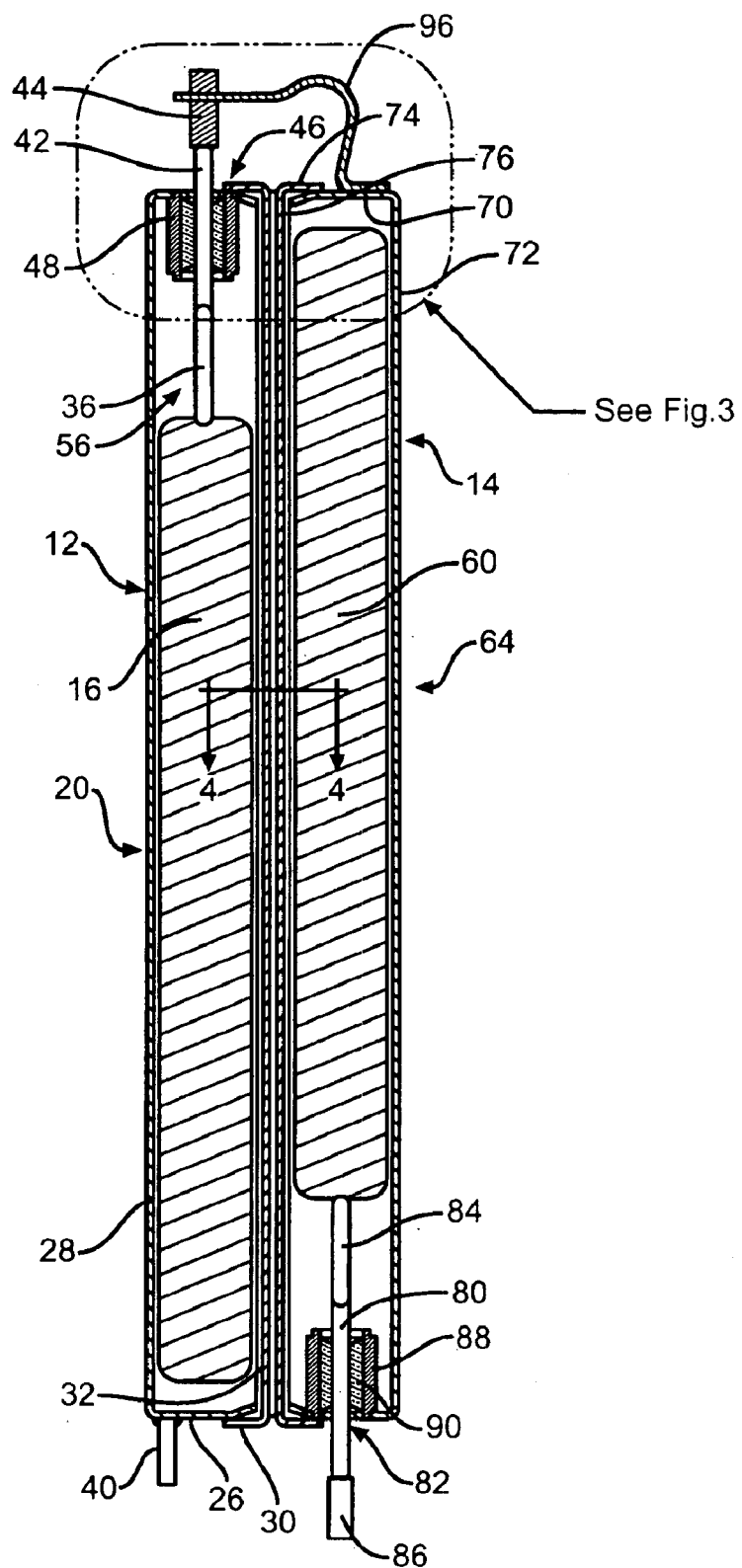
FIG. 2 is a cross-sectional view taken along line 2—2 of FIG. 1.
Figure 3:
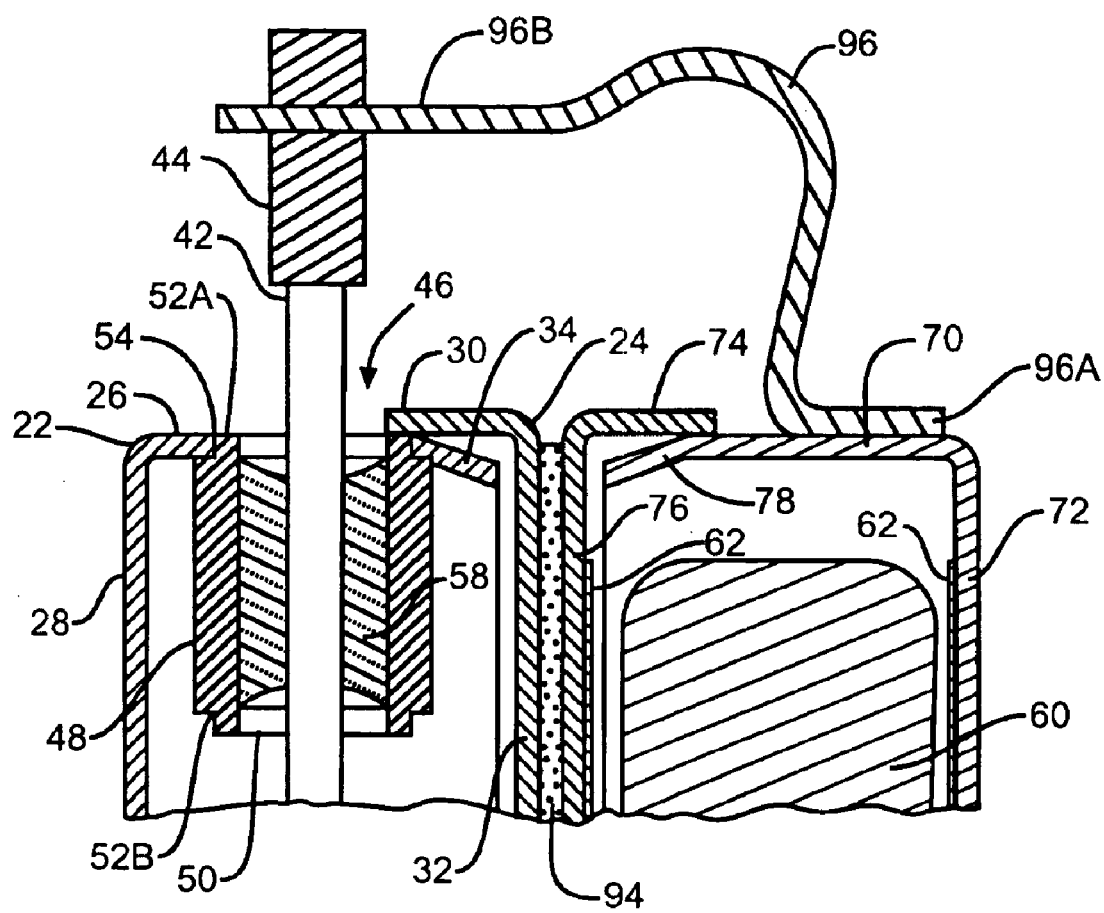
FIG. 3 is an enlarged view of the indicated area of FIG. 2.
Figure 4:
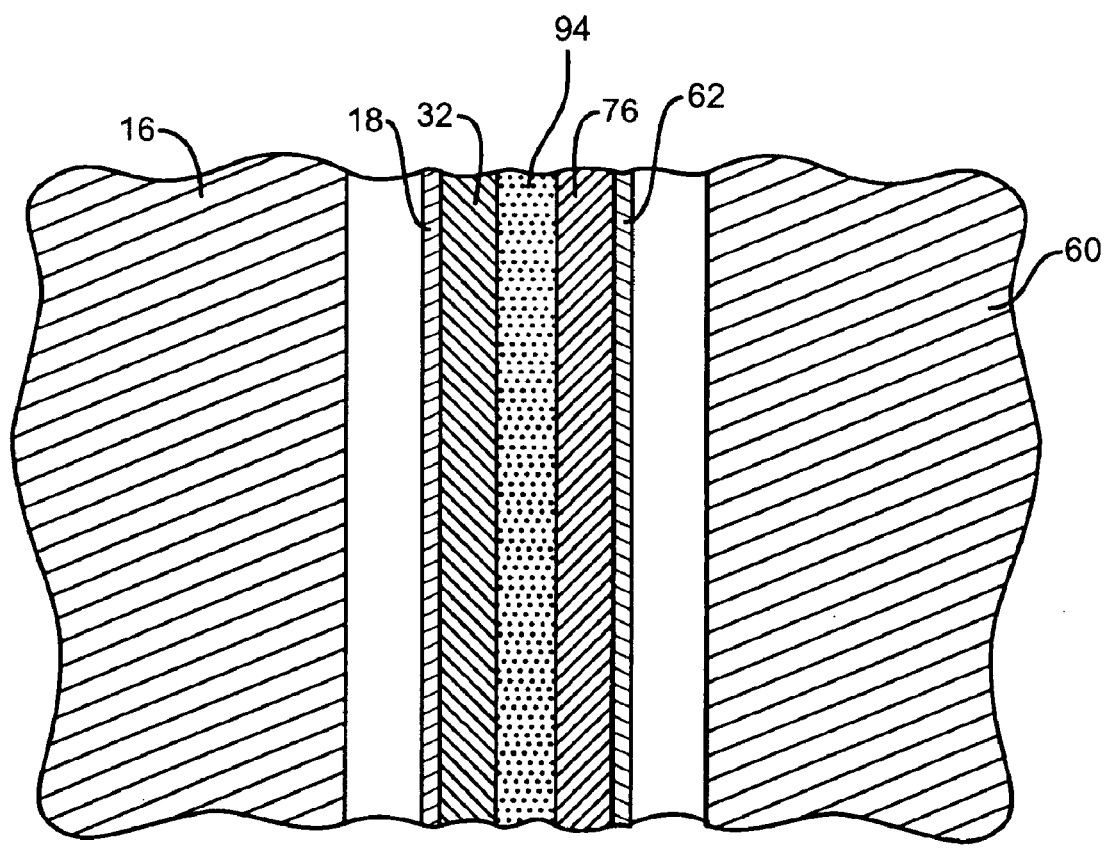
FIG. 4 is a cross-sectional view taken along line 4—4 of FIG. 2.

As shown in FIGS. 2 and 3, the anode lead 42 is electrically insulated from the metal casing 20 by an insulator glass-to-metal seal 46. The glass-to-metal seal 46 comprises a ferrule 48 defining an internal cylindrical through bore or passage 50 of constant inside diameter. Outwardly facing annular steps 52A and 52B are provided at the respective upper and lower ferrule ends. The upper step 52A is of an outer diameter sized to fit in a closely spaced relationship in an annular opening 54 in the first casing sidewall 26 with the remaining body of the ferrule butted against the inner surface of the sidewall. The ferrule 48 is secured therein by welding, and the like.

Figure 8:
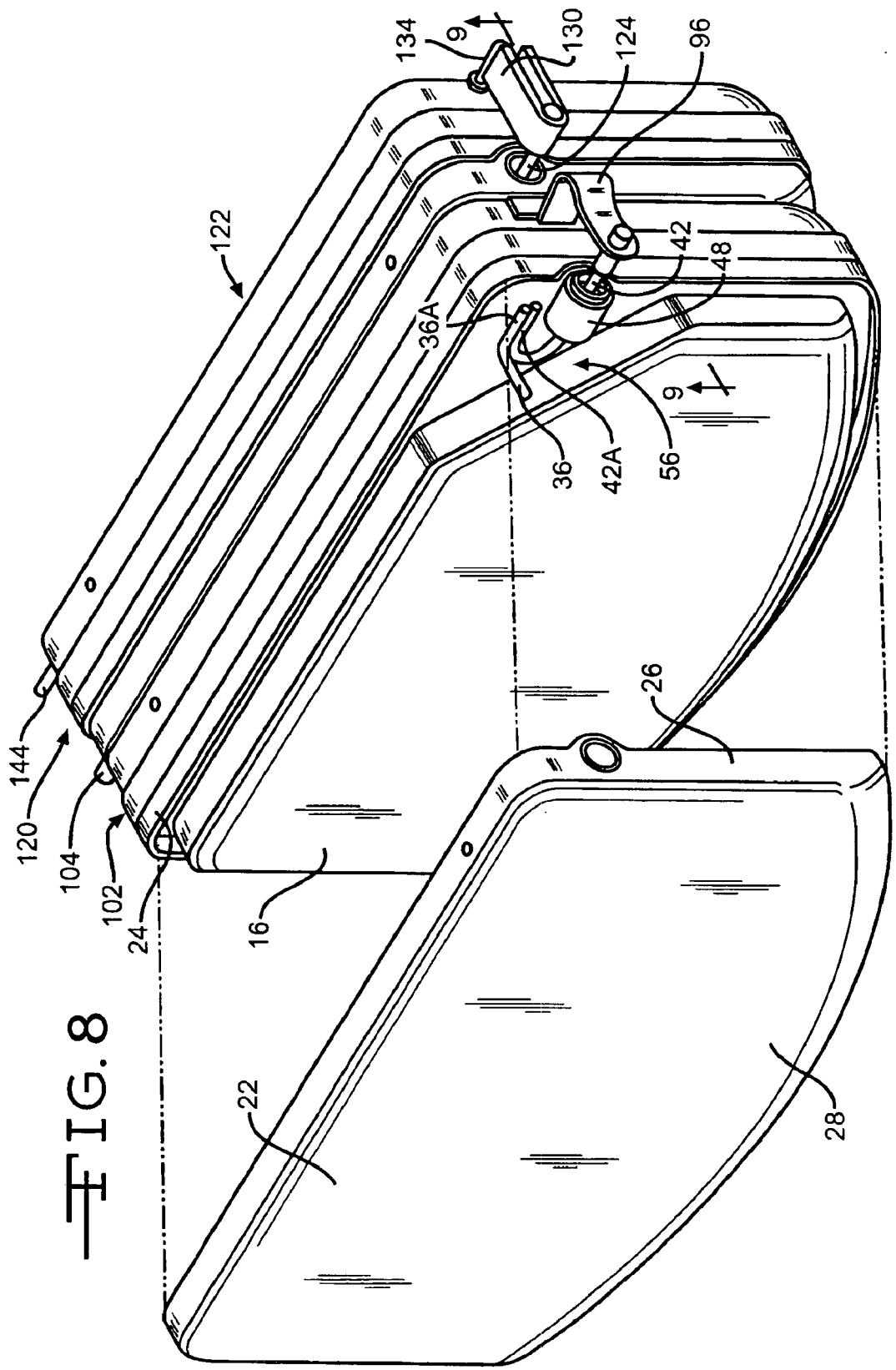
FIG. 8 is a partly exploded, perspective view of four side-by-side capacitors connected in series according to another embodiment of the present invention.
Figure 9:
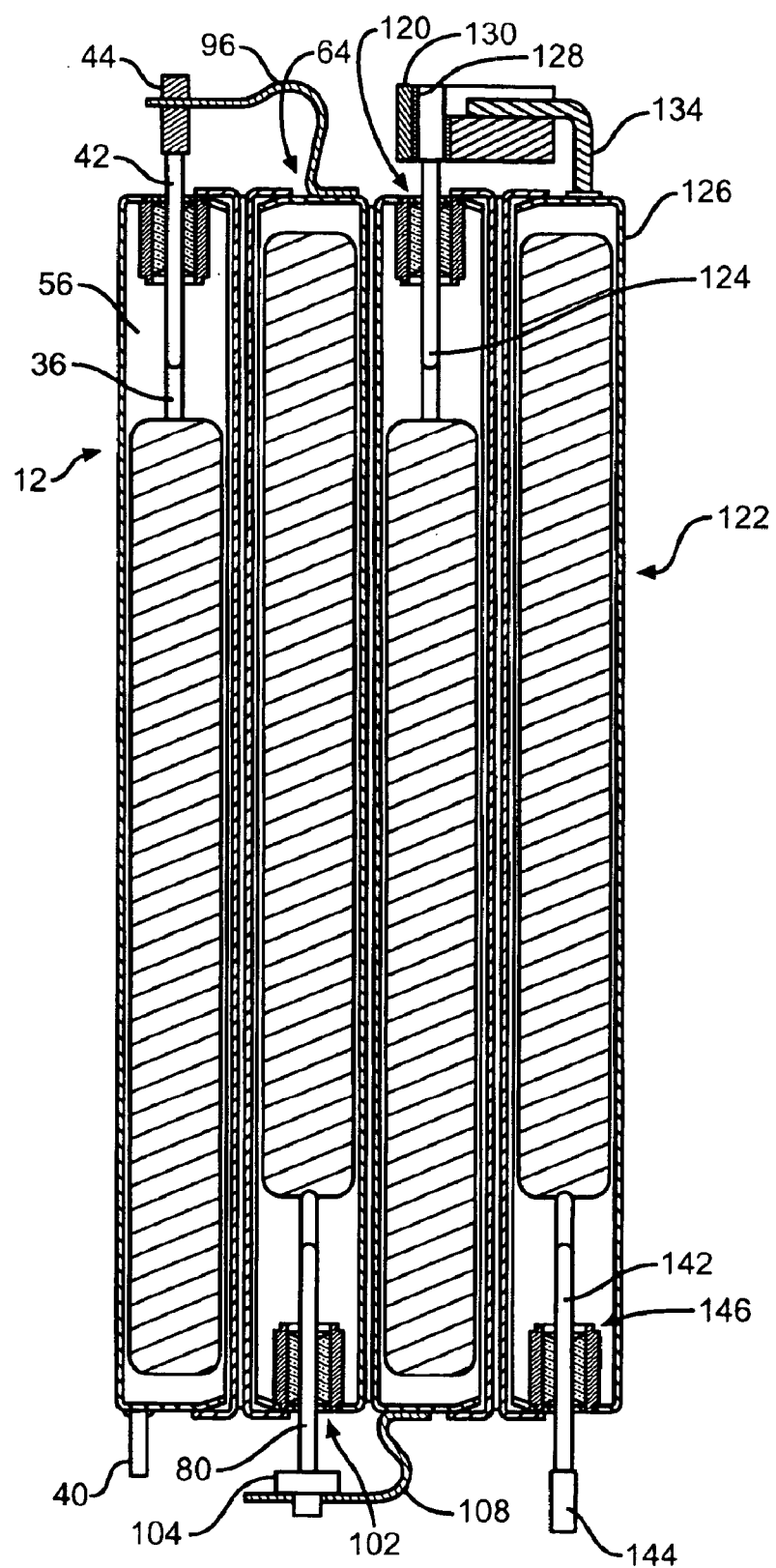
FIG. 9 is a cross-sectional view taken along line 9—9 of FIG. 8.

As shown in FIGS. 2, 8 and 9, the anode active material 16 has a notch 56 that provides clearance for the glass-to-metal seal 46. The anode wire 36 is embedded in the anode active material 16 extends outwardly from the notch 56. A distal end 36A is bent into a position generally parallel to the longitudinal axis of ferrule 48. A proximal end 42A of the anode lead 42 is bent into a J-hook shape to align parallel with the distal end 36A of the anode wire 36. The distal end 36A of the anode wire is then welded to the proximal end 42A of the anode lead to electrically connect the anode to the lead 42.

An insulative glass 58 provides a hermetic seal between the inside of the ferrule 48 and the anode lead 42. The glass is, for example, ELAN® type 88 or MANSOL™ type 88. The anode lead 42 preferably comprises the same material as the anode active material 16. In that manner, the portion of the anode lead 42 extending outside the capacitor 12 for connection to a load is hermetically sealed from the interior of the capacitor and insulated from the mating casing portions 22, 24 serving as the terminal for the cathode.

The second capacitor 14 illustrated in drawing FIGS. 1 to 4, 8 and 9 is similar to the first capacitor 12 in terms of its mechanical structure as well as its chemistry. As previously discussed, however, the capacitors 12, 14 need not be chemically similar. For example, the first capacitor 12 can be of an electrolytic type while the second capacitor 14 can be of the electrochemical type. Preferably, the capacitors 12, 14 are both of the electrolytic type.

The second capacitor 14 comprises an anode active material 60 and a cathode active material 62 (FIG. 3) housed inside a hermetically sealed casing 64 and operatively associated with each other by an electrolyte (not shown). Casing 64 is similar to casing 20 of capacitor 12 and comprises mating third and fourth portions 66 and 68 (FIG. 1). Casing portion 66 comprises a surrounding sidewall 70 extending to a face wall 72. Similarly, casing portion 68 comprises a surrounding sidewall 74 extending to a face wall 76. The sidewall 70 of the third casing portion 66 is sized to fit inside the periphery of the fourth sidewall 74 in a closely spaced relationship. The height of the fourth surrounding sidewall 74 is less than that of the third surrounding sidewall 70 and its inwardly angled lead-in portion 78. Laser welding the contacting sidewalls 70, 74 together hermetically seals the third and fourth mated casing portions 66, 68 to each other.

The cathode active material 62 is supported on the inner surfaces of the face walls 72, 76 opposite the major faces of the anode active material 60. In that manner, the casing 64, being of a conductive metal, serves as one terminal for making electrical connection between the capacitor 14 and its load.

The other electrical terminal or contact is provided by a conductor or lead 80 extending from within the capacitor 14 connected to the anode active material 60 and through the third surrounding sidewall 70. The anode active material 60 is similar in construction to the anode of capacitor 12 and includes a notch that provides clearance for a glass-to-metal seal 82. An anode wire 84 embedded in the anode active material 60 extends outwardly from the notch to a distal end welded to the proximal end of the anode lead 80 to electrically connect the anode to the lead.

The glass-to-metal seal 82 electrically insulates the anode lead 80 from the metal casing 64 and comprises a ferrule 86 provided with an annular step of reduced diameter fitted in a closely spaced relationship in an annular opening in the first casing sidewall 70. The remaining ferrule body is butted against the inner surface of the sidewall with the ferrule 86 being secured therein by welding. An insulative glass 88 hermetically seals between the cylindrical inner surface of the ferrule 86 and the anode lead 80.

A separator (not shown) of electrically insulative and ionically conductive material segregates the anode active material 60 from the cathode active material 62. The electrolyte is provided inside the hermetically sealed casing 64 through a fill opening closed by a hermetic closure 90.

The thusly constructed first and second capacitors 12, 14 are then positioned back-to-back or side-by-side. In this configuration, the face wall 32 of the casing portion 24 of the first capacitor 12 is aligned with and proximate to the face wall 76 of the casing portion 68 of the second capacitor 14. An adhesive 94 (FIG. 3), for example, a double-sided polyimide tape, is intermediate the casing portions 24, 68 to secure them together. A suitable tape for this purpose is commercially available from E. I. Du Pont De Nemours and Company Corporation under the trademark KAPTON®. If desired, the capacitors 12, 14 are provided with a paralyene coating by a vacuum deposition process about their entire outer surface prior to being aligned in the side-by-side orientation.

The capacitors 12, 14 are then electrically connected in series by a connecting tab 96. The tab 96 has a foot portion 96A secured to the surrounding sidewall 70 of casing portion 68, such as by welding, adjacent to the anode lead 42 for the first capacitor 12. An arm portion 96B of the tab has an opening that receives the sleeve 44 mounted on the distal end of the anode lead 42 in a surrounding relationship. A weld (not shown) then finishes the connection of the tab 96 to the sleeve 44 of the anode lead 42.

The positive polarity anode lead 42 of the first capacitor 12 is now connected to the negative polarity casing 64 of the second capacitor 14. The series connected side-by-side capacitors 12, 14 are then connectable to a load (not shown). Connecting the negative polarity terminal pin 40 of the first capacitor 12 and the sleeve 86 mounted on the positive polarity terminal lead 80 of the second capacitor 14 does this.

Figure 5:
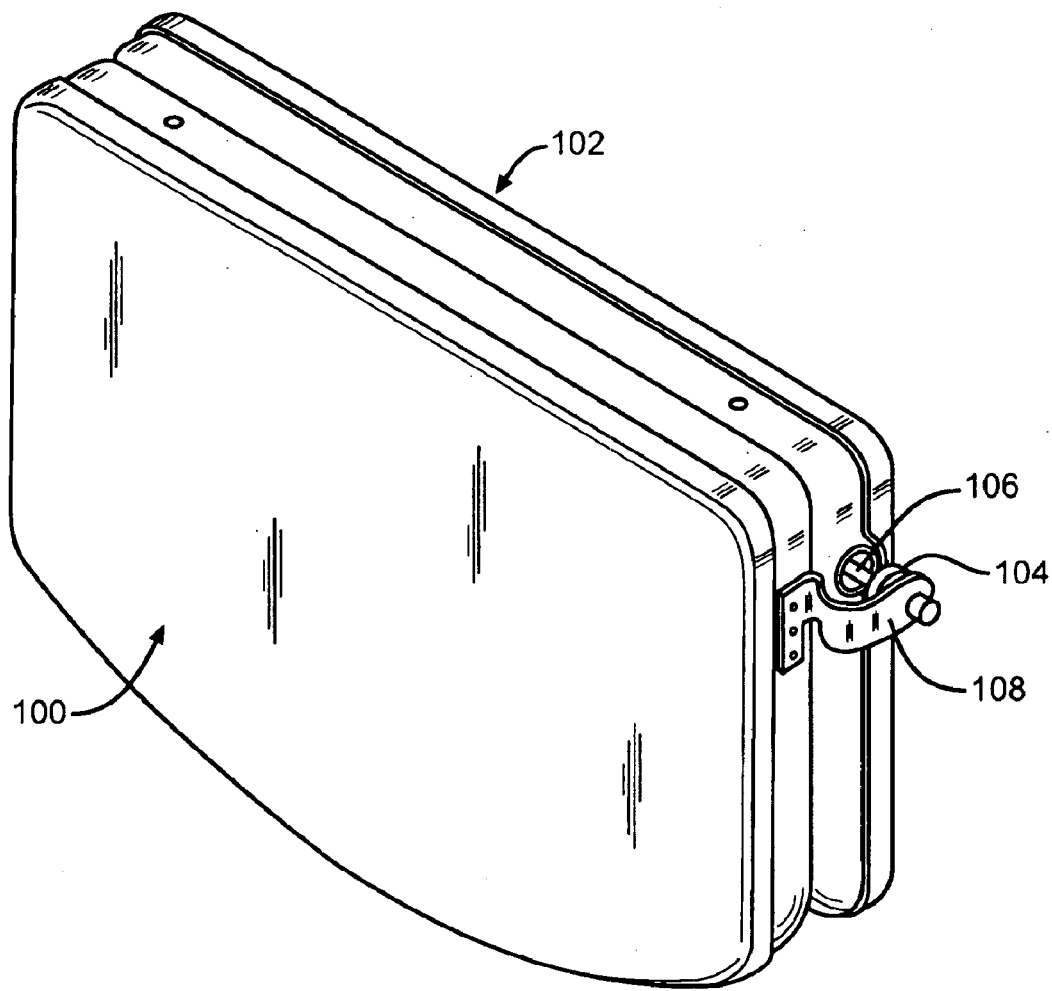
FIG. 5 is a perspective view looking at the right edges of two side-by-side capacitors connected in series according to another embodiment of the present invention.

FIG. 5 shows another embodiment for serially connecting side-by-side capacitors 100 and 102 according to the present invention. The capacitors 100, 102 are identical to the previously described capacitors 12, 14 in every respect except for the collared sleeve 104 mounted on the anode lead 106 of capacitor 102. This structure is particularly shown in FIG. 9 where the sleeve 86 mounted on the anode lead 80 for the capacitor 14 (FIG. 2) has been replaced by the collared sleeve 104. The collar 104 serves as a stop for properly aligning the arm portion 108A of a tab 108 when connecting it to the anode lead 80. The foot of tab 108 is connected to the casing 110 of an adjacent capacitor 102.

Figure 6:
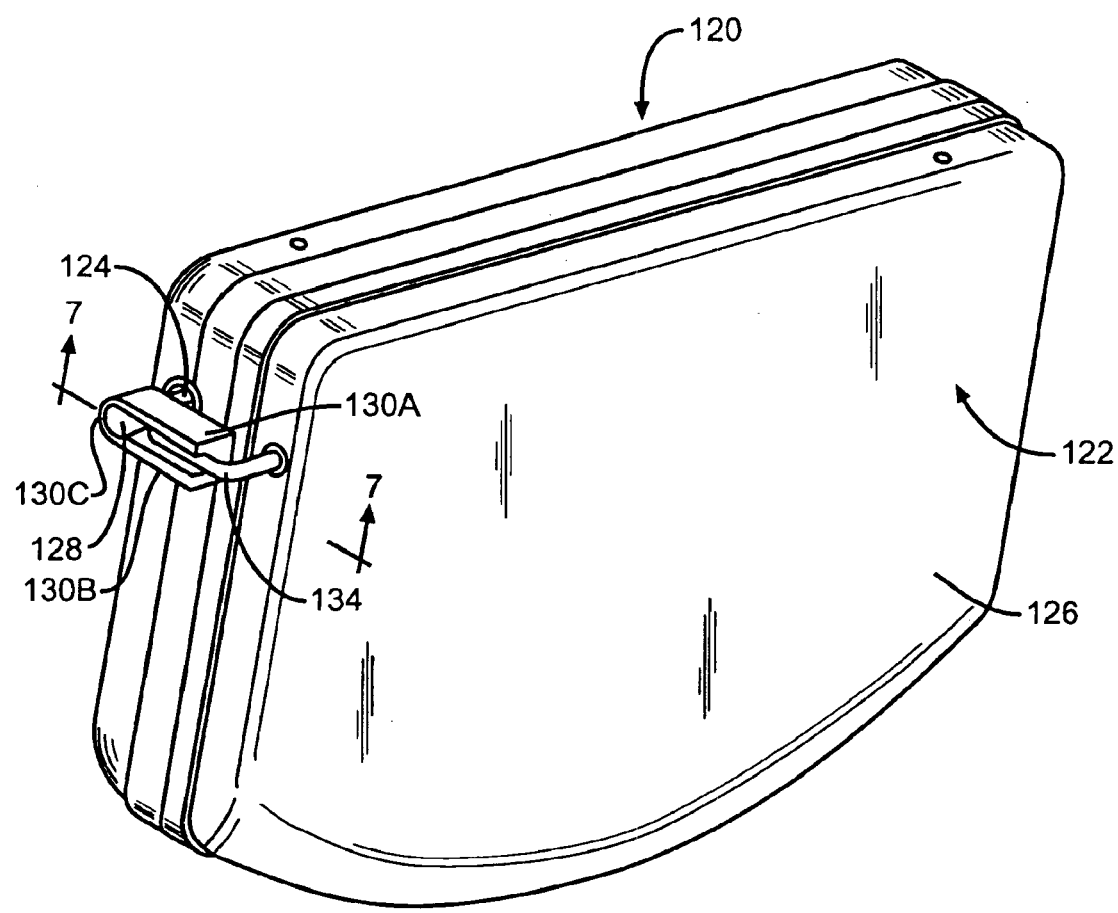
FIG. 6 is a perspective view looking at the left edges of two side-by-side capacitors connected in series according to another embodiment of the present invention.
Figure 7:
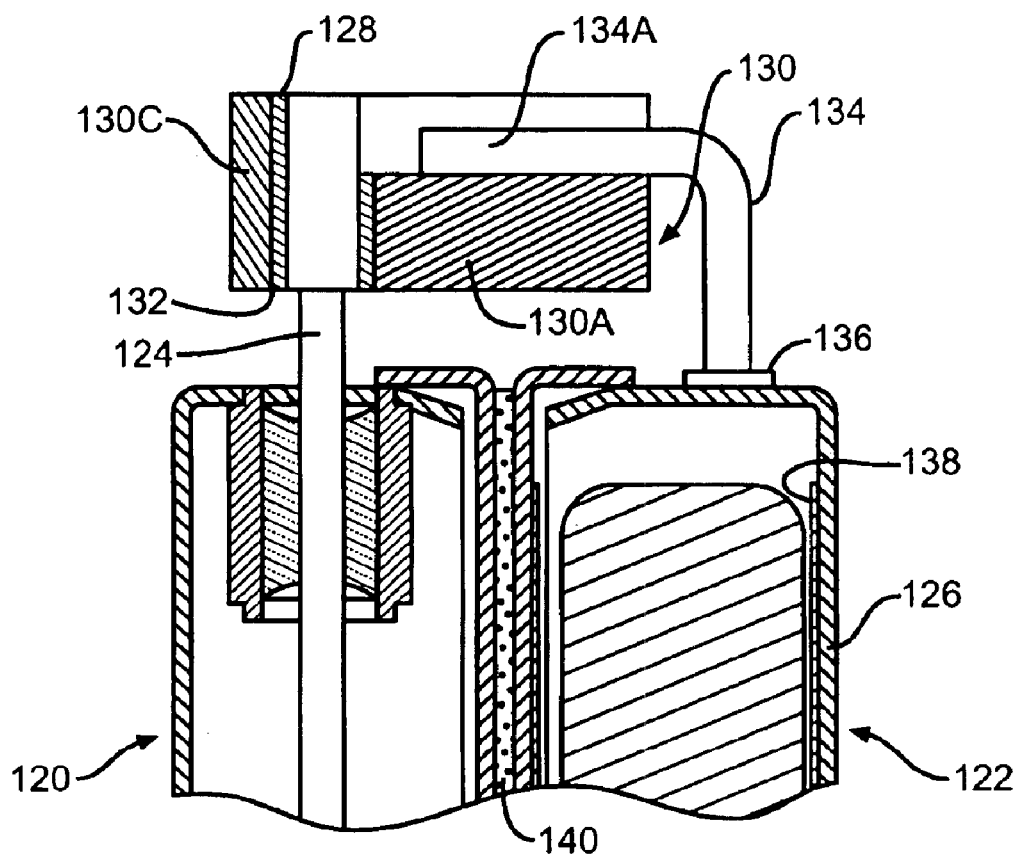
FIG. 7 is a cross-sectional view taken along line 7—7 of FIG. 6.

FIGS. 6 and 7 illustrate another embodiment for serially connecting side-by-side capacitors 120 and 122 according to the present invention. The capacitors 120, 122 are identical to the previously described capacitors 12, 14 in every respect except for the structure serially connecting the anode lead 124 of one to the casing 126 of the other.

The anode terminal lead 124 of capacitor 120 is provided with a sleeve 128 at its distal end thereof. The sleeve 128 supports a channel member 130 comprising a pair of spaced apart sidewalls 130A, 130B joined together by a closing end wall 130C. The channel 130 is open opposite the end wall 130C. The sidewalls 130A, 130B and end wall 130C meet at a bottom wall provided with an opening 132 that snuggly receives the sleeve 128 of the anode lead 124. The sleeve 128 and channel member 130 are connected together, such as by crimping. Alternatively, a solder or weld (not shown) is used to make the connection.

An angled terminal pin 134 is provided with an enlarged base 136 secured to the sidewall 138 of the casing 126 for capacitor 122, such as by welding. A distal portion 134A of the terminal pin 134 is formed by a right-angled bend. That way, when the capacitors 120, 122 are brought together into the side-by-side orientation contacting the double-sided adhesive tape 140, the distal portion 134A of the terminal pin 134 is received in the channel member 130 between its sidewalls 130A, 130B. Crimping, soldering or welding the channel sidewalls onto the terminal pin 134 then makes the connection between the capacitors 120, 122.

FIG. 9 illustrates an embodiment of the present invention where the sleeve 44 mounted on the positive polarity anode lead 42 of capacitor 12 is connected to the negative polarity casing 64 of capacitor 14 by the tab 96. The collared sleeve 104 mounted on the positive polarity lead 80 of capacitor 102 is connected to the negative polarity casing of capacitor 120 by the tab 108 resting against the collar. The sleeve 128 on the positive polarity terminal lead 124 of capacitor 120 is, in turn, connected to the negative polarity casing 126 of the capacitor 122 by the angled terminal pin 134 received in the channel member 130. A positive polarity terminal lead 142 provided with a distal sleeve 144 is electrically insulated from the casing 126 for the capacitor 122 by a glass-to-metal seal 146. The terminal lead 142 and glass-to-metal seal 144 are similar to those that have been previously described.

Thus, according to the present invention, adjacent capacitors are connectable in series by connecting the anode terminal lead from one to the casing of the next. The anode terminal lead can be connected to the next capacitor's casing by a sleeve 44/tab 96 structure, a collared sleeve 104/tab 108 structure, or a sleeve 128/channel member 130 structure. That way, any number of capacitors is serially connected together to increase the delivered capacity of the assembly. This is particularly important in advanced implantable medial devices, such as cardiac defibrillators, where delivered capacity coupled with reduced package volume is paramount in the minds of design engineers.

It is appreciated that various modifications to the inventive concepts described herein may be apparent to those of ordinary skill in the art without departing from the spirit and scope of the present invention as defined by the appended claims.

What is claimed is:

1. A capacitor assembly, which comprises:
    a) a first capacitor having a first anode and a first cathode operatively associated with each other by an electrolyte contained inside a first casing, wherein one of the first anode and the first cathode is connected to the first casing as its terminal and the other of the first anode and the first cathode comprises a first lead extending outside the first casing and insulated therefrom;
    b) a second capacitor having a second anode and a second cathode operatively associated with each other by an electrolyte contained inside a second casing, wherein the one of the second anode and the second cathode that is of the opposite polarity as that of the first anode and the first cathode connected to the first casing is connected to a second lead extending outside the second casing and insulated therefrom and the other of the second anode and the second cathode is connected to the second casing as its terminal; and
    c) a first electrical connector extends from the first lead of the first capacitor to the second casing to thereby electrically connect the first and second capacitors in series.

2. The capacitor assembly of claim 1 wherein the electrical connector is a tab having a foot portion secured to second casing and an arm portion secured to the first lead.

3. The capacitor assembly of claim 2 wherein the arm portion of the tab comprises an opening that receives the first lead in a surrounding relationship.

4. The capacitor assembly of claim 2 wherein the first lead has a collar and wherein the arm portion of the tab comprises an opening that receives the first lead in a surrounding relationship with the arm portion abutting the collar.

5. The capacitor assembly of claim 1 wherein the electrical connector comprises a second lead extending from the second casing and wherein one of the first lead and the second lead supports a channel member having spaced apart sidewalls that electrically connect to the other of the first and second leads when the sidewalls are moved into contact with the lead.

6. The capacitor assembly of claim 1 wherein the first and second series connected capacitors are positioned side-by-side with an adhesive disposed therebetween.

7. The capacitor assembly of claim 1 wherein the first casing comprises first and second casing portions, the first casing portion comprising a first face wall extending to a surrounding first sidewall and the second casing portion comprises a second face wall extending to a surrounding second sidewall with the first sidewall sealed to the second sidewall and wherein the second casing comprises third and fourth casing portions, the third casing portion comprising a third face wall extending to a surrounding third sidewall and the fourth casing portion comprising a fourth face wall extending to a surrounding fourth sidewall with the third sidewall sealed to the fourth sidewall, and wherein the first and second series connected capacitors are positioned with the first face wall proximate to and aligned with the third face wall.

8. The capacitor assembly of claim 1 wherein a pin is secured to the first casing as a connection for the one of the first anode and the first cathode connected to the casing.

9. The capacitor assembly of claim 1 wherein a third capacitor comprises a third anode and a third cathode operatively associated with each other by an electrolyte contained inside a third casing, wherein the one of the third anode and the third cathode that is of the opposite polarity as that of the second anode and the second cathode connected to the second casing is connected to a third lead extending outside the third casing and insulated therefrom and the other of the third anode and the third cathode is connected to the third casing as it terminal, and wherein a second electrical connection extends from the second lead of the second capacitor to the third casing to thereby electrically connect the second and third capacitors in series.

10. The capacitor assembly of claim 9 wherein a fourth capacitor comprises a fourth anode and a fourth cathode operatively associated with each other by an electrolyte contained inside a fourth casing, wherein the one of the fourth anode and the fourth cathode that is of the opposite polarity as that of the third anode and the third cathode connected to the third casing is connected to a fourth lead extending outside the fourth casing and insulated therefrom and the other of the fourth anode and the fourth cathode is connected to the fourth casing as it terminal, and wherein a third electrical connection extends from the third lead of the third capacitor to the fourth casing to thereby electrically connect the third and fourth capacitors in series.

11. A method for providing a first capacitor and a second capacitor electrically connected to each other in series, comprising the steps of:

a) providing a first capacitor comprising a first anode and a first cathode operatively associated with each other by an electrolyte, wherein one of the first anode and the first cathode is connected to the first casing as its terminal and the other of the first anode and the first cathode comprises a first lead extending outside the first casing and insulated therefrom;

b) providing a second capacitor comprising a second anode and a second cathode operatively associated with each other by an electrolyte contained inside a second casing, wherein the one of the second anode and the second cathode that is of the opposite polarity as that of the first anode and the first cathode connected to the first casing is connected to a second lead extending outside the second casing and insulated therefrom and the other of the second anode and the second cathode is connected to the second casing as it terminal; and c) securing a first end of an electrical connector to the first lead of the first capacitor and a second end of the electrical connector to the second casing.

12. The method of claim 11 including providing a third capacitor comprising a third anode and a third cathode operatively associated with each other by an electrolyte contained inside a third casing, and connecting the one of the third anode and the third cathode that is of the opposite polarity as that of the second anode and the second cathode connected to the second casing to a third lead extending outside the third casing and insulated therefrom and connecting the other of the third anode and the third cathode to the third casing as it terminal, and further connecting a second electrical connection from the second lead of the second capacitor to the third casing to thereby electrically connect the second and third capacitors in series.

13. The method of claim 12 including providing a fourth capacitor comprising a fourth anode and a fourth cathode operatively associated with each other by an electrolyte contained inside a fourth casing, and connecting the one of the fourth anode and the fourth cathode that is of the opposite polarity as that of the third anode and the third cathode connected to the third casing to a fourth lead extending outside the fourth casing and insulated therefrom and connecting the other of the fourth anode and the fourth cathode to the fourth casing as it terminal, and further connecting a third electrical connection from the third lead of the third capacitor to the fourth casing to thereby electrically connect the third and fourth capacitors in series.

14. The method of claim 11 including securing a foot portion of a tab to the second casing and an arm portion of the tab to the first lead.

15. The method of claim 14 including providing the arm portion of the tab comprises an opening receiving the first lead in a surrounding relationship.

16. The method of claim 14 including providing the first lead comprising a collar and providing the arm portion of the tab comprising an opening receiving the first lead in a surrounding relationship with the arm portion abutting the collar.

17. The method of claim 11 including providing the electrical connector comprising a second lead extending from the second casing with one of the first lead and the second lead supporting a channel member having spaced apart sidewalls and electrically connecting the channel member to the other of the first and second leads by moving the sidewalls into contact with the lead.

18. The method of claim 11 including positioning the first and second series connected capacitors side-by-side with an adhesive disposed therebetween.

19. The method of claim 11 including providing the first casing comprising first and second casing portions, the first casing portion comprising a first face wall extending to a surrounding first sidewall and the second casing portion comprises a second face wall extending to a surrounding second sidewall and sealing the first sidewall to the second sidewall and providing the second casing comprising third and fourth casing portions, the third casing portion comprising a third face wall extending to a surrounding third sidewall and the fourth casing portion comprising a fourth face wall extending to a surrounding fourth sidewall and sealing the third sidewall to the fourth sidewall, and positioning the first and second series connected capacitors with their respective first and third face walls proximate to and aligned with each other.

20. The method of claim 11 including securing a pin to the first casing as a connection for the one of the first anode and the first cathode connected to the casing.

\* \* \* \* \*